United States Patent
May

(10) Patent No.: US 9,682,179 B2
(45) Date of Patent: Jun. 20, 2017

(54) DEVICE FOR VACUUM TREATMENT OF WOUNDS

(75) Inventor: Alexander May, Passau (DE)

(73) Assignee: BSN MEDICAL GMBH, Hamburg (DE)

( * ) Notice: Subject to any disclaimer, the term of this patent is extended or adjusted under 35 U.S.C. 154(b) by 440 days.

(21) Appl. No.: 14/119,829

(22) PCT Filed: May 30, 2012

(86) PCT No.: PCT/EP2012/060101
§ 371 (c)(1),
(2), (4) Date: Jan. 30, 2014

(87) PCT Pub. No.: WO2012/163943
PCT Pub. Date: Dec. 6, 2012

(65) Prior Publication Data
US 2014/0303575 A1    Oct. 9, 2014

(30) Foreign Application Priority Data

Jun. 1, 2011 (DE) .................. 10 2011 110 705

(51) Int. Cl.
| | | |
|---|---|---|
| A61M 5/00 | (2006.01) | |
| A61M 1/00 | (2006.01) | |
| A61M 5/32 | (2006.01) | |
| A61M 35/00 | (2006.01) | |
| A61M 5/178 | (2006.01) | |

(52) U.S. Cl.
CPC ........ *A61M 1/0025* (2014.02); *A61M 1/0001* (2013.01); *A61M 1/0088* (2013.01); *A61M 2205/587* (2013.01)

(58) Field of Classification Search
CPC .......... A61M 5/00; A61M 5/32; A61M 35/00; A61M 1/00; A61M 5/178; A61F 7/00
See application file for complete search history.

(56) References Cited

U.S. PATENT DOCUMENTS

| | | |
|---|---|---|
| 3,572,340 A | 3/1971 | Lloyd et al. |
| 6,174,306 B1 | 1/2001 | Fleischmann |
| 6,261,276 B1 | 7/2001 | Reitsma |
| 7,276,052 B2 | 10/2007 | Kobayashi et al. |
| 7,532,953 B2 | 5/2009 | Vogel |
| 7,611,500 B1 | 11/2009 | Lina et al. |
| 7,670,323 B2 | 3/2010 | Hunt et al. |

(Continued)

FOREIGN PATENT DOCUMENTS

JP         3034369 U      2/1997

OTHER PUBLICATIONS

International Search Report (PCT/EP2012/060101) 3 pages.
JP Official Action of Oct. 30, 2015—Japanese with English translation.

*Primary Examiner* — Tatyana Zalukaeva
*Assistant Examiner* — Ilya Treyger
(74) *Attorney, Agent, or Firm* — The Maxham Firm

(57) ABSTRACT

A device for vacuum treatment of wounds, the device having a disposable canister for receiving a suctioned wound exudate, and a vacuum pump. The disposable canister is designed to partially enclose the vacuum pump, which is inserted into the canister, and to thereby fix it against movements in non-inserting directions. The structure of the device is used mainly in a stationary mode and occasionally is used in a mobile mode when worn by patients.

2 Claims, 1 Drawing Sheet

(56) References Cited

U.S. PATENT DOCUMENTS

| | | | |
|---|---|---|---|
| 7,837,673 B2 | 11/2010 | Vogel | |
| 7,931,651 B2 | 4/2011 | Webb et al. | |
| 8,048,046 B2 * | 11/2011 | Hudspeth | A61M 1/0088 604/119 |
| 8,142,405 B2 | 3/2012 | Vogel | |
| 8,641,693 B2 * | 2/2014 | Locke | A61M 1/0001 206/438 |
| 8,657,806 B2 * | 2/2014 | Eckstein | A61M 1/0023 15/325 |
| 2002/0082569 A1 | 6/2002 | Wildman | |
| 2005/0080384 A1 | 4/2005 | Green, Jr. | |
| 2007/0299411 A1 | 12/2007 | Vogel | |
| 2007/0299412 A1 | 12/2007 | Vogel | |
| 2008/0294109 A1 | 11/2008 | Estes et al. | |
| 2009/0240218 A1 | 9/2009 | Braga et al. | |
| 2010/0106112 A1 | 4/2010 | Vogel | |
| 2011/0040288 A1 | 2/2011 | Eckstein et al. | |
| 2011/0054810 A1 | 3/2011 | Turner et al. | |

\* cited by examiner

DEVICE FOR VACUUM TREATMENT OF WOUNDS

FIELD OF INVENTION

The concept disclosed herein relates generally to a device for vacuum treatment of wounds, and more particularly to a compact apparatus where a disposable canister confines the vacuum pump.

BACKGROUND OF THE INVENTION

Principles of the subject of vacuum treatment of wounds are described in U.S. Pat. No. 3,572,340, for example. Here, a container partially evacuated by a vacuum pump withdraws ichor via a drainage port from a wound which was filled by a wound foam such as an open-celled polyurethane foam and was sealed by means of a film so as to be air-tight. As a result, the ichor is drained from the oozing wound and collected in the container which is typically made as a disposable canister. The wound then remains moist in the sense of modern wound care approach. The granulation of a wound is accelerated by the vacuum therapy of wounds. On the average, the wound thus already closes after about 28 days. Very large-area wounds have to be treated for a correspondingly longer period of time.

The vacuum therapy of wounds is used for deep and also flat (superficial) wounds. For this purpose, different wound fillers are correspondingly offered. The suction vacuum produced by the pump must be adapted to the type of wound. In a normal case, wounds are treated by a reduced pressure of 80-120 mmHg (110-169 hPa). Above all, a continuous or an intermittent suction is used among the possible temporal suction pressure patterns. The continuous suction mode of operation proves advantageous with respect to the patient's experience of pain. The tissue is here treated continuously so as to exclude an undesired relief of the tissue.

The canister for receiving the wound exudate is usually mounted on the pump housing in such a way that it is attached to a side of the pump housing or at least partially surrounded by it. Such vacuum treatment devices of wounds are known, for example, from German patent specifications DE 69505545 T2 for a stationary use and DE 69629507 T2 for a mobile use. A further application of the vacuum treatment of wounds is described in U.S. Pat. No. 7,931,651.

SUMMARY OF EMBODIMENTS OF THE INVENTION

One of the purposes of embodiments of this invention is to provide pump and disposable canister designs which advantageously comply with requirements regarding a stationary mode and an occasionally mobile use of such a device, and do it in a cost-effective manner as compared with known devices of this type.

According to embodiments of the invention, the disposable canister has a recess in which the pump can at least partially be inserted. The walls of the recess enclose the pump to such an extent that the pump is thus fixed to the disposable canister in two dimensions and is only movable in the direction of insertion. The pump is fixed to the canister with respect to this direction of movement by an additional closure. The pump housing thus advantageously has no recesses which are hard to access for cleaning purposes and have pointed interior angles for receiving the canister. Having been filled, the canister, which is basically relatively difficult to clean, is disposed of rather than cleaned.

The type and position of the canister in relation to the pump has an effect on the maintenance friendliness in the replacement of a full canister, on the readability of the filling level of an at least partially transparent canister and on the wearing comfort of the vacuum treatment apparatus of wounds which consists of pump and canister on a patient's body when it is used in a mobile mode.

In an advantageous embodiment of the invention, the canister is formed and the recess in the canister is positioned so as to balance out the device consisting of the canister and the pump which is inserted therein. This combination can be attached to the patient's body by means of a two-point suspension in such a way that the tensile forces are always approximately equal at both suspension points due to the weight distribution of the device, irrespective of the canister filling when the canister is disposed in a normal horizontal operating position. This increases the wearing comfort on the body when the device is worn with a belt attached to the two suspension points.

In an advantageous embodiment of the invention, this is achieved by making the canister approximately symmetrical relative to the mirror plane which mirrors the two suspension points into each other, wherein the recess for the pump is further approximately cut in half by the mirror plane.

In another advantageous embodiment of the invention, the canister is transparent at least in an area of an outer wall and is provided with a filling level indicator where its filling level can be directly read.

In a further advantageous embodiment of the invention, the canister is also transparent at least in one area of the canister recess wall, that area being opposite to the transparent outer wall of the canister. This allows a lighting to be set into the pump surface to directly illuminate the filling level scale when the pump is fixed in the canister and the lighting is turned on. This improves the readability of the filling level by increasing the contrast when the lighting conditions are poor.

In an advantageous embodiment of the invention, the color of lighting is chosen in the visible spectral range which is absorbed by the wound exudate in the best possible way.

BRIEF DESCRIPTION OF THE DRAWING

The objects, advantages, and features of the embodiments of the invention will be more clearly perceived from the following detailed description, when read in conjunction with the accompanying drawing, in which.

DETAILED DESCRIPTION OF EMBODIMENTS OF THE INVENTION

Figure 1:
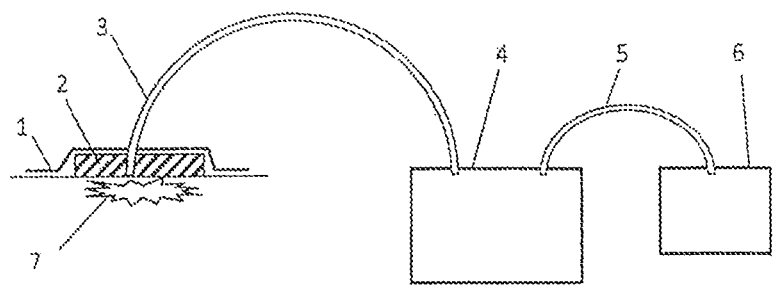
FIG. 1 is a schematic diagram of prior art treatment of wounds.

FIG. 1 shows the functional principles of known vacuum treatment of wounds. A wound 7 is covered with wound filler 2 which is sealed using film 1 so as to be air-tight. From this the wound secretion is sucked into container 4 through drainage hose 3, the container being partially evacuated in a controlled fashion via connection 5 using vacuum pump 6.

Figure 2:
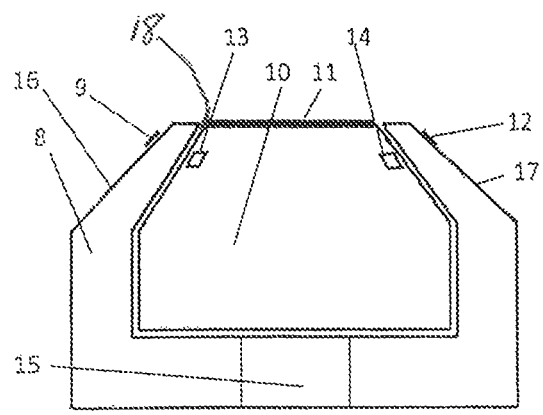
FIG. 2 is a top view of the apparatus of an embodiment of the inventive concept.

FIG. 2 shows a top view of the apparatus of a preferred exemplary embodiment of the invention.

Figure 3:
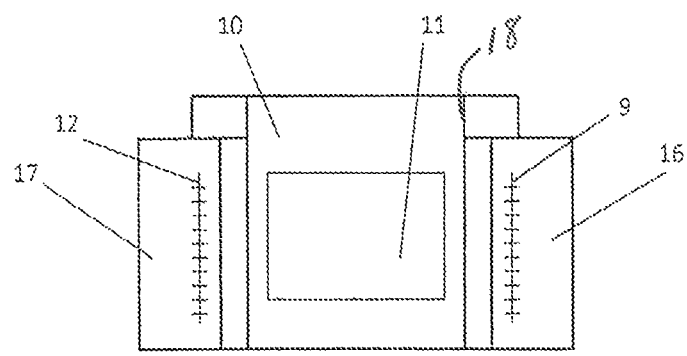
FIG. 3 is a front view of the apparatus of FIG. 2.

FIG. 3 is a view of the embodiment of the apparatus of FIG. 2 from the front with a view to operating panel 11 attached to pump 10 in the form of a touch panel. Pump 10 is secured against shift in a horizontal plane by a canister 8 partially enclosing it. For this purpose, canister 8 encloses pump 10 with the exception of a recess 18 serving for operating touch panel 11 from all sides, except from the top side front where the pump is inserted into the canister. Filling level scales 9, 12 are attached to inclined sides 16, 17 of canister 8. By this means the filling level of the wound exudate can be read from both the front with a view to the touch panel and from the side. Alternatively, at least one filling level scale 9, 12 is irradiated with direct lighting 13, 14 on opposite sides of the pump housing, if required. The lighting is preferably made as an LED or OLED cell and is selectively energizable. In an exemplary preferred embodiment, the thickness of canister 8 in the area of filling level scale 9, 12 is less than the predominant other thickness of the canister. Further, inclined sides 16, 17 are generally transparent, at least in die areas of the lighting elements and scales so that the scales may be illuminated and viewed from the external surfaces of inclined sides 16, 17. This serves for avoiding an insufficient lighting of the filling level scale 9, 12 resulting from an excessive absorption by the canister filling material which binds the vacuumed-off wound exudate when the light passes through the canister.

While scales 9, 12 are shown on the outside of inclined canister sides 16, 17, the scales could be on the inside or embedded within the inclined sides, which are generally transparent in the area of the scales and lighting elements 13, 14.

In order to be able to easily remove the pump from the canister in one-handed fashion, the canister has an additional recess 15 on the opposite side facing away from operating panel 11 of the pump, the recess serving for gripping the pump by a thumb or finger of a person.

In a further advantageous exemplary design, the canister side winch is opposite to operating panel 11 of the pump and which abuts against the body during a mobile operation, is curved toward the patient's body and therefore the contact surface with the body is increased. The apparatus can thus be better fixed to the body and the wearing comfort is improved.

While canister 8 is characterized as being transparent, only the inclined sides 16, 17 may be transparent so that filling level scales 9, 12 are visually effective.

What is claimed is:

1. Apparatus for vacuum treatment of wounds, the apparatus comprising:
   a vacuum pump;
   disposable canister for receiving wound exudate, the canister being formed with a recess for receiving the vacuum pump therein, the canister and the vacuum pump being connectable to each other in such a way that the vacuum pump is only movable in the direction of insertion, wherein when so connected, the canister encloses the entire vacuum pump from all sides with the exception of the side from which the vacuum pump is inserted into the canister, the vacuum pump being formed with an operating panel, the canister being formed with a recess providing access to the operating panel, the canister having an additional recess at a side facing away and opposite to the operating panel of the vacuum pump, through which additional recess the vacuum pump is shaped to be gripped by a person's thumb, wherein a closure at the canister and the vacuum pump secures the vacuum pump in the canister with respect to a shift in the direction of insertion;
   the canister is formed with sides that are at least partially transparent;
   at least one fill level scale mounted to at least one of the at least partially transparent sides of the canister; and
   a lighting element mounted on the vacuum pump and aligned in such a way that it directly illuminates the filling level scale mounted to the transparent side of the canister when the vacuum pump is connected with the canister.

2. The apparatus according to claim 1, wherein:
   the canister has upper inclined sides formed to at least partially enclose the vacuum pump, the inclined sides being transparent and fill level scales are mounted on outer sides of the inclined sides; and
   the vacuum pump has lighting elements on both sides which are selectively energizable and align with the fill level scales to illuminate the scales when the vacuum pump is inserted into the recess in the canister.

* * * * *